United States Patent [19]

Oda et al.

[11] Patent Number: 4,721,825

[45] Date of Patent: *  Jan. 26, 1988

[54] PROCESS FOR THE PRODUCTION OF XYLENE

[75] Inventors: Sumihiro Oda; Haruhito Sato, both of Sodegaura, Japan

[73] Assignee: Idemitsu Kosan Company Limited, Tokyo, Japan

[*] Notice: The portion of the term of this patent subsequent to May 28, 2002 has been disclaimed.

[21] Appl. No.: 618,461

[22] Filed: Jun. 8, 1984

[30] Foreign Application Priority Data

Jun. 17, 1983 [JP] Japan .................. 58-107890
Jul. 13, 1983 [JP] Japan .................. 58-126225

[51] Int. Cl.$^4$ .................................. C07C 2/68
[52] U.S. Cl. ......................... 585/462; 585/467; 585/463
[58] Field of Search ............. 585/462, 463, 467; 502/77

[56] References Cited

U.S. PATENT DOCUMENTS

| | | | |
|---|---|---|---|
| 3,354,078 | 11/1967 | Miale et al. | 585/467 |
| 3,417,148 | 12/1968 | Fishel | 585/467 |
| 3,436,432 | 4/1969 | Mitsche | 585/467 |
| 3,692,697 | 9/1972 | Kravitz | 585/467 |
| 4,060,568 | 11/1978 | Rodewald | 502/71 |
| 4,090,981 | 5/1978 | Rodewald | 502/71 |
| 4,100,215 | 7/1978 | Chen | 585/467 |
| 4,100,217 | 7/1978 | Young | 585/467 |
| 4,292,457 | 9/1981 | Klotz | 585/467 |
| 4,361,713 | 11/1982 | Kalding | 585/467 |
| 4,427,786 | 1/1984 | Miale et al. | 502/77 |
| 4,427,787 | 1/1984 | Miale et al. | 502/77 |
| 4,427,789 | 1/1984 | Miale et al. | 502/77 |
| 4,444,900 | 4/1984 | Chang et al. | 502/71 |
| 4,500,421 | 2/1985 | Chang et al. | 585/408 |
| 4,520,219 | 5/1985 | Sato | 585/462 |
| 4,530,756 | 7/1985 | Chang et al. | 585/408 |
| 4,577,048 | 3/1986 | Chang et al. | 585/467 |

FOREIGN PATENT DOCUMENTS 984380 2/1965 United Kingdom ............ 585/467

*Primary Examiner*—William R. Dixon, Jr.
*Assistant Examiner*—Cynthia A. Prezlock
*Attorney, Agent, or Firm*—Frishauf, Holtz, Goodman & Woodward

[57] ABSTRACT

A process for producing xylene from toluene or benzene by the use as a catalyst of a fluorine-containing crystalline aluminosilicate or a fluorine-containing crystalline borosilicate. The specified crystalline silicate catalyst increases the conversion of toluene or benzen and the selectivity of xylene. This catalyst can keep its high catalytic activity for long periods of time during the reaction.

20 Claims, No Drawings

PROCESS FOR THE PRODUCTION OF XYLENE

BACKGROUND OF THE INVENTION

The present invention relates to a proces for the production of xylene, more particularly to a process for producing xylene from toluene or benzene in high selectivity by using fluorine-containing crystalline aluminosilicate or fluorine-containing crystalline borosilicate as a catalyst.

Various processes have been known to produce xylene, which is industrially very useful, by methylation of toluene or benzene. For example, a process of methylation in the presence of crystalline aluminosilicates such as ZSM-5 and ZSM-11 is disclosed in Japanese patent application laid-open Nos. 57688/1976 and 120292/1977, and a process of methylation using crystalline borosilicate is disclosed in Japanese patent application laid-open No. 55500/1978.

When, however, these crystalline aluminosilicates such as ZSM-5 are used with no modification as catalysts in the methylation of toluene, undesirable side reactions such as disproportionation are liable to occur. This will lead to a reduction in selectivity of xylene. Furthermore, the crystalline aluminosilicate catalysts are inferior in respect of durability or service life and are not sufficiently satisfactory for practical use.

Similarly, when the crystalline borosilicate catalyst is used as it is, the methylating agent is not effectively used in the methylation reaction and side reactions occur, yielding large amounts of by-products.

SUMMARY OF THE INVENTION

An object of the invention is to provide a process for producing xylene with high selectivity.

Another object of the invention is to provide catalysts for use in the production of xylene which can keep their high catalytic activity over long periods of time.

It has been found that the objects are attained by using fluorine-containing crystalline aluminosilicates or fluorine-containing crystalline borosilicates as the catalyst.

The present invention relates to a process for producing xylene by methylation of toluene or benzene in the presence of a catalyst, which is characterized in that a fluorine-containing crystalline aluminosilicate or fluorine-containing crystalline borosilicate is used as the catalyst.

DETAILED DESCRIPTION OF THE INVENTION

Fluorine-containing crystalline aluminosilicates as used herein can be prepared by introducing fluorine into crystalline aluminosilicates by procedures as described hereinafter. Various types of crystalline aluminosilicates can be used, of which are preferred those aluminosilicates in which the silica/alumina molar ratio is at least 12/1, especially from 20/1 to 400/1, and the constraint index is from 1 to 12, especially from 5 to 10.

The silica/alumina molar ratio is determined by a conventional method of analysis. The constraint index is as defined in J. Catal., 67, 218 (1981).

The constraint index is a criterion which is applied in judging whether or not a given aluminosilicate has properties for controlling the passage of molecules having greater cross sections than n-paraffins through the aluminosilicate. The constraint index can be easily determined by continously introducing a mixture of equal amounts of n-hexane and 3-methylpentane over the aluminosilicate sample under atmospheric pressure according to a series of steps as described in J. Catal., 67, 218 (1981). The constraint index is defined as follows:

$$\text{Constraint Index} = \frac{\log_{10} \text{(proportion of remaining n-hexane)}}{\log_{10} \text{(proportion of remaining 3-methylpentane)}}$$

Aluminosilicates as used herein, as described above, preferably have a constraint index falling within the range of from 1 to 12. If the constraint index is less than 1, the pore diameter is too large and by-products such as trimethylbenzene are formed, resulting in a reduction in sensitivity of xylene. On the other hand, if the constraint index is in excess of 12, the pore diameter is too small and the methylation of toluene or benzene proceeds only insufficiently.

Any aluminosilicates having a silica/alumina molar ratio and a constraint index falling within the above-specified ranges can be preferably used in the present invention. Examples are aluminosilicates such as ZSM-5, ZSM-11, ZSM-12, ZSM-23, ZSM-35, ZSM-38 and ZSM-48.

These aluminosilicates are subjected to a fluorination treatment to yield the corresponding fluorine-containing crystalline aluminosilicates. This fluorination treatment is sufficient where fluorine is introduced into an aluminosilicate, yielding a fluorinated aluminosilicate. The fluorination treatment can be performed in various manners. For example, an aluminosilicate is contacted with a gaseous fluorine compound at a temperature of from 400° to 600° C., or with compounds such as hydrofluoric acid, ammonium fluoride, sodium fluoride, boron trifluoride and monofluoroacetic acid in a liquid phase. Various types of gaseous fluorine compound can be used, including organic fluorine compounds such as fluorohydrocarbon, chlorofluorohydrocarbon, chlorofluorocarbon, and fluorocarbon. Examples of the gaseous fluorine compound are furon-11 ($CFCl_3$), furon-12 ($CF_2Cl_2$), furon-13 ($CF_3Cl$), furon-21 ($CHFCl_2$), furon-22 ($CHF_2Cl$), furon-23 ($CHF_3$), furon-113 ($CF_2ClCFCl_2$), and furon-114 ($CF_2ClCF_2Cl$). The fluorine-containing crystalline aluminosilicates prepared by using the organic fluorine compounds are preferable since they can keep high catalytic activity for long periods of time during the reaction.

The fluorine-containing crystalline aluminosilicates can be also prepared by adding a silica source an alumina source, and a crystallization agent such as alkyl ammonium salt (e.g. tetra-n-propylammonium bromide) to an aqueous medium and subjecting the resulting aqueous mixture to a hydrothermal reaction in the presence of a fluorine compound such as hydrofluoric acid and sodium fluoride.

The silica source used herein is not subject to any special limitation; for example, powdered silica, silicic acid, colloidal silica, and dissolved silica can be used. Examples of such dissolved silicas include water glass containing 1 to 5 moles of $SiO_2$ per mole of $Na_2O$ or $K_2O$, silicate, and alkali metal silicate.

Various compounds can be used as the alumina source, including alumina sulfate, sodium aluminate, colloidal alumina, and alumina.

If aluminosilicates are used in the methylation of toluene or benzene without application of a fluorination treatment as described above, the selectively of xylene is not sufficiently high and the catalytic life is short, rendering them unsuitable for practical use.

Fluorine-containing crystalline borosilicates can be prepared by applying a florination treatment onto crystalline borosilicates. Various types of crystalline borosilicates can be used, including the crystalline borosilicates described in Japanese patent application Laid-Open Nos. 55500/1978, 7598/1980, 84313/1981, 123817/1982, and 129820/1982. These crystalline borosilicates can be prepared by various procedures. In generaly, they can be prepared by adding a silica source, a boron source, and a crystallization agent to an aqueous medium and subjecting the resulting mixture to a hydrothermal reaction. The silica source and the crystallization agent herein may be the same as in the preparation of the crystalline aluminosilicate described above. The boron source includes boric acid, metaboric acid, anhydrous boric acid, tetraboric acid and borate. For example, an ammonium form of crystalline borosilicate is prepared as follows:

An aqueous solution (Solution A) containing boric acid, concentrated sulfuric acid and tetrapropylammonium bormide, an aqueous solution (Solution B) of water glass comprising silicon oxide, sodium oxide and water, and an aqueous solution (Solution C) of sodium chloride are prepared separately. Solutions A and B are added dropwise to Solution C. The resulting mixture, if necessary after adjusting to a given pH value, is heated in an autoclave. Thereafter it is cooled, washed, dried and calcined whereupon crystalline sodium borosilicate is obtained. This crystalline sodium borosilicate is then converted into an ammonium form of borosilicate by treating with an aqueous solution of ammonium nitrate. The thus-prepared borosilicate is in powder form but can be molded by addition of binders such as alumina sol.

If the above-prepared crystalline borosilicate is used as a catalyst without application of any treatment, the selectively of xylene is low and the catalyst cannot keep its high catalytic activity for long periods of time during the reaction.

For this reason, the process of the present invention uses fluorine-containing borosilicates which are prepared by applying a fluorination treatment onto crystalline borosilicates as prepared above. This fluorination treatment is sufficient when fluorine introduced into crystalline borosilicates, yielding fluorine-containing borosilicates. This fluorination treatment can be performed in various manners. For example, a crystalline borosilicate is contacted with the gaseous fluorine compound as described above at a temperature of from 400° to 600° C., or with compounds such as hydrofuoric acid, ammonium fluoride, sodium fluoride, boron trifluoride and monofluoroacetic acid in a liquid phase. Alternatively, in preparing crystalline borosilicates, a fluorine source may be added along with a silica source, a boron source, a crystallization agent, and so forth, the resulting aqueous mixture being subjected to a hydrothermal reaction whereupon fluorine is introduced simuiltaneously with the formation of crystalline borosilicates. In this case, as the fluorine source, liquid compounds such as hydrofluoric acid and sodium fluoride are preferably used.

The above-prepared fluorine-containing crystalline aluminosilicate or fluorine-containing crystalline borosilicate is molded singly or in admixture with a suitable binder such as alumina and then calcined at a temperature of from 550° to 1,000° C. This molded product is used as a catalyst in the production of xylene according to the present invention.

The starting material used in the process of the present invention is toluene, benzene or a mixture thereof. The methylating agent is not subject to any special limitations. For example, methanol, dimethyl ether, methyl chloride, and methyl bromide can be used. Particularly preferred is methanol. The amount of the methylating agent being used can be determined appropriately depending on the type of the starting material, the reaction conditions, and so forth. Usually the molar ratio of the starting material to the methylating agent is from 1/10 to 20/1, with the range of from 1/2 to 5/1 being preferred.

There are no special limitations on other reaction condisstions in the practice of the process of the present invention. In general, the reaction is performed at a temperature of from 200° to 650° C., preferably from 400° to 600° C. under a pressure of from atmospheric pressure to 20 kilograms per square centimeter (gauge) ($kg/cm^2G$), preferably from atmospheric pressure to 10 $kg/cm^2G$ at a weight hourly space velocity (WHSV) of from 0.1 to 50 per hour, preferably from 0.5 to 20 per hour.

The present invention offers various advantages over conventional processes in the production of xylene from benzene or toluene. For example, side reactions such as decomposition of the methylating agent are prevented, resulting in an increase in the conversion of toluene and selectivity of xylene. The service life of the catalyst used in the present invention can be carried out continuously over long periods of time while keeping high catalytic activity.

Thus the process of the present invention is very useful as a process for industrial production of xylene.

The present invention is described in greater detail with reference to the following examples and comparative examples.

EXAMPLE 1

(1) Preparation of Catalyst

Aluminum sulfate (7.5 grams) was dissolved in 250 milliliters of water, and further 17.6 grams of concentrated sulfuric acid and 26.3 grams of tetra-n-propylammonium bromide were dissolved therein to prepare Solution A. Separately, 211.0 grams of water glass (J Sodium Silicate No. 3, produced by Nippon Kagaku Kogyo Co., Ltd.) was dissolved in 250 milliliters of water to prepare Solution B. Moreover, 79.0 grams of sodium chloride was dissolved in 122 milliliters of water to prepare Solution C.

Solutions A and B were added dropwise simultaneously to Solution C at room temperature over 10 minutes. The resulting mixture was placed in an autoclave and heated at 170° C. for 20 hours. The contents, after being cooled, were filtered off, washed with water, and then dried at 120° C. for 12 hours. X-ray diffraction analysis showed that the product was ZSM-5.

ZSM-5 as prepared above was calcined at 550° C. for 6 hours to yield 56.5 grams of a sodium form of ZSM-5. This sodium form of ZSM-5 was added to a 5-fold amount (by weight) of a 1 normal aqueous solution of ammonium nitrate, and the resulting mixture was refluxed for 8 hours. At the end of the time, the reaction mixture was cooled, allowed to stand, and the supernatant was removed by decantation. The operation of reflux and decantation was repeated further three times. The contents were filtered off, washed with water, and then dried at 120° C. for 12 hours to yield an ammonium form of ZSM-5. For the thus-produced zeolite, $SiO_2/Al_2O_3=90/1$ (molar ratio) and the constrain index (CI value) of the proton form was 8.

To this ammonium form of ZSM-5 was added alumina sol as a binder so that the alumina content (as determined after calcination) was 20% by weight. The mixture was pelletized, dried at 120° C. for 16 hours, and then calcined at 550° C. for 6 hours. A reaction tube was charged with 6.5 grams of the above-prepared pellets. Furon-114 (1,1,2,2-tetrafluoro1,2-dichloroethane) was fed to the reaction tube at 550° C. at a rate of 70 milliliters per minute for 1 hour to achieve a fluorination treatment, whereupon the desired fluorine-containing catalyst was obtained.

(2) Methylation of Toluene

An atmospheric pressure fixed-bed flow type reaction tube was charged with 2 grams of the catalyst prepared in (1) above, and a feedstock comprising toluene and methanol (toluene/methanol=4/1 (molar ratio)) was introduced into the reaction tube at a weight hourly space velocity (WHSV) of 9 per hour and reacted. The results are shown in Table 1.

EXAMPLE 2 determined after calcination) was 20% by weight. The mixture was molded, dried at 120° C. for 16 hours, and then calcined at 550° C. for 6 hours.

A reaction tube was charged with 6.5 grams of the calcined pellets. Furon-13 (trifluorochloromethane) was fed to the reaction tube at 500° C. at a rate of 70 milliliters per minute over 1 hour to achieve a fluorination treatment, whereupon the desired fluorine-containing catalyst was obtained.

(2) Methylene of Toluene

The procedure of (2) in Example 1 was repeated wherein the catalyst prepared in (1) above was used in place of the catalyst of Example 1. The results are shown in Table 1.

COMPARATIVE EXAMPLE 1

(1) Preparation of Catalyst

A catalyst was prepared in the same manner as in Example 1 (1) except that the fluorination treatment using furon-114 was not applied.

(2) Methylation of Toluene

The procedure of (2) in Example 1 was repeated wherein the catalyst as prepared in (1) above was used in place of the catalyst of Example 1. The results are shown in Table 1.

TABLE 1

| Run No. | 2 Hours from the start of the reaction | | 14 Hours from the start of the reaction | | 26 Hours from the start of the reaction | |
|---|---|---|---|---|---|---|
| | Conversion of toluene (%) | Selectivity of xylene (%) | Conversion of toluene (%) | Selectivity of xylene (%) | Conversion of toluene (%) | Selectivity of xylene (%) |
| Example 1 | 24 | 92 | 23 | 93 | 21 | 95 |
| Example 2 | 22 | 91 | 20 | 94 | 18 | 95 |
| Comparative Example 1 | 27 | 77 | 2 | 63 | 0 | — |

(1) Preparation of Catalyst

Aluminum sulfate (7.5 grams) was dissolved in 250 milliliters of water, and 17.6 grams of concentrated sulfuric acid and 31.3 grams of tetra-n-butylammonium bromide were dissolved therein to prepare Solution A. Separately, 211.0 grams of water glass (same as used in Example 1) was dissolved in 250 milliliters of water to prepare Solution B. Solutions A and B were simultaneously dropped to 122 milliliters of water at room temperature over 10 minutes.

The mixture was placed in an autoclave and heated at 170° C. for 20 hours. The contents, after being cooled, were filtered off, washed with water, and then dried at 120° C. for 12 hours. X-ray diffraction analysis showed that the product was ZSM-11.

ZSM-11 as prepared above was calcined at 550° C. for 6 hours to yield 57.7 grams of a sodium form of ZSM-11. This sodium form of ZSM-11 was added to a 5-fold amount (by weight) of a 1 normal aqueous solution of ammonium nitrate, and the resulting mixture was refluxed for 8 hours. The reaction mixture was cooled, allowed to stand, and the supernatant was removed by decantation. The operation of reflux and decantation was repeated further three times. The contents were filtered off, washed with water, and dried at 120° C. for 12 hours to yield an ammonium form of ZSM-11. For the thus-prepared zeolite, $SiO_2/Al_2O_3=90/1$ (molar ratio) and the CI value of the proton form was 8.

To this ammonium form of ZSM-11 was added an alumina sol as a binder so that the alumina content (as

EXAMPLE 3

(1) Preparation of Catalyst

Solution A was prepared by adding 0.29 gram of boric acid, 3.9 grams of concentrated sulfuric acid, and 5.8 grams of tetra-n-propylammonium bromide to 55 milliliters of water; Solution B was prepared by adding 46.9 grams of water glass (J Sodium Silicate No. 3, produced by Nippon Kagaku Kogyo Co., Ltd.) to 55 milliliters of water; and Solution C was prepared by adding 17.4 grams of sodium chloride to 27 milliliters of water.

Solutions A and B were added dropwise simultaneously to Solution C. The resulting solution was placed in an autoclave and heated at 170° C. for 20 hours. The contents, after being cooled, were filtered off, washed with water, and dried at 120° C. for 12 hours. Furthermore, they were calcined at 550° C. for 6 hours to yield 13.4 grams of a sodium form of crystalline borosilicate. X-ray diffraction analysis showed that the product was of the ZSM-5 structure.

Borosilicate as prepared above was added to a 5-fold amount (by weight) of a 1 normal aqueous solution of ammonium nitrate, and the resulting mixture was refluxed for 8 hours. At the end of the time, the solids were filtered off. The operation of reflux and filtration was applied further three times onto the solids which were then washed with water and dried at 120° C. for 12 hours, whereupon there was obtained an ammonium form of crystalline borosilicate.

To this borosilicate was added an alumina sol so that the alumina content (as determined after calcination) was 20% by weight. The mixture was molded, dried at 120° C. for 12 hours, and further calcined at 550° C. for 6 hours to yield a proton form of crystalline borosilicate mold.

A reaction tube was charged with 2 grams of the above-prepared mold, to which 1,1,2,2-tetrafluoro-1,2-dichloroethane (furon-114) was fed for 3 hours at a rate of 70 milliliters per minute while maintaining the temperature at 500° C. to achieve a fluorination treatment. There was thus obtained the desired fluorine-containing crystalline borosilicate.

(2) Methylation of Toluene

An atmospheric pressure fixed-bed flow type reaction tube was charged with 2 grams of the fluorine-containing crystalline borosilicate prepared in (1) above, and a feedstock comprising toluene and methanol (toluene/methanol=4/1 (molar ratio)) was fed thereto and reacted at a temperature of 600° C. and a weight hourly space velocity (WHSV) of 9.2 per hour. The results are shown in Table 2.

COMPARATIVE EXAMPLE 2

(1) Preparation of Catalyst

A proton form of crystalline borosilicate mold was prepared in the same manner as in Example 3 (1) except that the fluorination treatment was not applied.

(2) Methylation of Toluene

The methylation of toluene was carried out in the same manner as in Example 3 (2) except that the mold prepared in (1) above was used as the catalyst. The results are shown in Table 2.

TABLE 2

| Run No. | Conversion of toluene (%) | Selectivity of xylene (%) | Amount of gas formed (milliliter per hour)* |
|---|---|---|---|
| Example 3 | 26 | 93 | 30 |
| Comparative Example 2 | 22 | 92 | 100 |

Note:
*Composed mainly of carbon monoxide, hydrogen and methane due to decomposition of methanol.

EXAMPLE 4

(1) Preparation of Catalyst

Solution A was prepared by adding 0.29 gram of boric acid and 3.9 grams of concentrated sulfuric acid to 23 milliliters of water; and Solution B was prepared by adding 46.9 grams of water glass (J Sodium Silicate No. 3, produced by Nippon Kagaku Kogyo Co., Ltd.) to 21 milliliters of water. Solutions A and B were simultaneously dropped to 11 milliliters of water, and 83 milliliters of methanol was then added thereto.

The resulting mixture was placed in an autoclave and heated at 170° C. for 20 hours. The contents, after being cooled, were filtered off, washed with water, dried at 120° C. for 12 hours, and then calcined at 550° C. for 6 hours to yield 11.5 grams of a sodium form of crystalline borosilicate. X-ray diffraction analysis showed that the product was of the ISI-1 type structure (see Japanese patent application laid-open No. 135124-1983).

The above-prepared borosilicate was added to a 5-fold amount (by weight) of a 1 normal aqueous solution of hydrochloric acid. The resulting mixture was heated at 70° C. for 8 hours, cooled, and then filtered. The thus-obtained solids were subjected further three times to the operation of heating and filtration under the same conditions as above and, thereafter, washed with water and dried at 120° C. for 12 hours to yield a proton form of crystalline borosilicate.

To this borosilicate was added an alumina sol so that the alumina content (as determined after calcination) was 20% by weight. The mixture was molded, dried for 12 hours, and then calcined at 550° C. for 6 hours to yield a proton form of crystalline borosilicate mold.

A reaction tube was charged with 2 grams of the above-prepared mold, to which 1,1,2,2-tetrafluoro-1,2-dichloroethane (furon-114) was fed for 3 hours at a rate of 70 milliliters per minute while maintaining the temperature at 500° C. to achieve a fluorination treatment. There was thus obtained the desired fluorine-containing crystalline borosilicate.

(2) Methylation of Toluene

An atmospheric pressure fixed-bed flow type reaction tube was charged with 2 grams of the fluorine-containing crystalline borosilicate prepared in (1) above as the catalyst, to which a feedstock comprising toluene and methanol (toluene/methanol=4/1 (molar ratio)) was fed and reacted at a temperature of 600° C. and a weight hourly space velocity (WHSV) of 2 per hour. The results are shown in Table 3.

COMPARATIVE EXAMPLE 3

(1) Preparation of Catalyst

A proton form of crystalline borosilicate mold was prepared in the same manner as in Example 4 (1) except that the fluorination treatment was not applied.

(2) Methylation of Toluene

The methylation of toluene was performed in the same manner as in Example 4 (2) except that the mold prepared in (1) above was used as the catalyst. The results are shown in Table 3.

TABLE 3

| Run No. | Conversion of toluene (%) | Selectivity of xylene (%) |
|---|---|---|
| Example 4 | 14 | 94 |
| Comparative Example 3 | 2 | 63 |

What is claimed is:

1. In an improved process for producing xylene by contacting toluene or benzene with a methylating agent in the presence of a catalyst whereby said toluene or benzene is methylated to form xylene, said methylation being carried out at a temperature of from 200° C. to 650° C., the improvement comprising using as said catalyst (i) a fluorine-containing crystalline borosilicate or (ii) a fluorine-containing crystalline aluminosilicate having a silica/alumina molar ratio of at least 12/1 and a Constraint index of from 1 to 12.

2. The process as claimed in claim 1, wherein said catalyst is said fluorine-containing crystalline aluminosilicate and has a silica/alumina molar ratio of from 20/1 to 400/1 and a constraint index of from 5 to 10.

3. The process as claimed in claim 1, wherein said catalyst is said fluorine-containing crystalline aluminosilicate and said catalyst is prepared by contacting a crystalline aluminosilicate with a fluorine compound.

4. The process as claimed in claim 3, wherein the fluorine compound is a compound selected from the group consisting of fluorohydrocarbon, chlorofluorohydrocarbon, chlorofluorocarbon, fluorocarbon, hydrofluoric acid, ammonium fluoride, sodium fluoride, boron trifluoride, monofluoroacetic acid, and a mixture thereof.

5. The process as claimed in claim 3, wherein the fluorine compound is an organic fluorine compound.

6. The process as claimed in claim 5, wherein the organic fluorine compound is fluorohydrocarbon, chlorofluorohydrocarbon, chlorofluorocarbon or fluorocarbon.

7. The process as claimed in claim 1, wherein said catalyst is said fluorine-containing crystalline aluminosilicate and said catalyst is prepared by subjecting an aqueous mixture of a silica source, an alumina source and a crystallization agent to a hydrothermal reaction in the presence of a fluorine compound.

8. The process as claimed in claim 7, wherein the fluorine compound is hydrofluoric acid, sodium fluoride, potassium fluoride, ammonium fluoride, fluorosilicic acid or fluorosilicic acid salt.

9. The process as claimed in claim 1, wherein said catalyst is said fluorine-containing crystalline borosilicate and said catalyst is prepared by contacting a crystalline borosilicate with a fluorine compound.

10. The process as claimed in claim 9 wherein the fluorine compound is a compound selected from the group consisting of fluorohydrocarabon, chlorofluorohydrocarbon, chlorofluorocarbon, fluorocarbon, hydrofluoric acid, ammonium fluoride, sodium fluoride, boron trifluoride, monofluoroacetic acid, and a mixture thereof.

11. The process as claimed in claim 1, wherein said catalyst is said fluorine-containing crystalline borosilicate and said catalyst is prepared by subjecting an aqueous mixture of a silica source, a boron source and a crystallization agent to a hydrothermal reaction in the presence of a fluorine compound.

12. The process as claimed in claim 11, wherein the fluorine compound is hydrofluoric acid or sodium fluoride.

13. The process as claimed in claim 1, wherein the methylation of toluene or benzene is carried out by the use of one or more methylating agents selected from methanol, dimethyl ether, methyl chloride, and methyl bromide.

14. The process as claimed in claim 13, wherein the molar ratio of toluene or benzene to the methylating agent is from 1/10 to 20/1.

15. The process as claimed in claim 1, wherein the methylation reaction is carried out at 200° to 650° C., atmospheric pressure up to 20 kilograms per square centimeter (gauge), and weight hourly space velocity (WHSV) of 0.1 to 50 per hour.

16. The process as claimed in claim 1, wherein the methylation is carried out by the use of one or more methylating agents selected from methanol, dimethyl ether, methyl chloride, and methyl bromide; the molar ratio of toluene or benzene to the methylating agent is from 1/10 to 20/1; the methylation reaction is carried out at an atmospheric pressure up to 20 kilograms per square centimeter (gauge), and weight hourly space velocity (WHSV) of 0.1 to 50 per hour.

17. The process as claimed in claim 16, wherein said fluorine-containing crystalline aluminosilicate is prepared by contacting a crystalline aluminosilicate with a fluorine compound and said fluorine compound is selected from the group consisting of fluorohydrocarbon, chlorofluorohydrocarbon, chlorofluorocarbon or fluorocarbon.

18. The process as claimed in claim 8, wherein said fluorine-containing crystallin aluminosilicate has a silica/alumina molar ratio of from 20/1 to 40/1 and a Constraint index of from 5 to 10; and wherein the methylation is carried out by the use of one more methylating agents selected from methanol, dimethyl ether, methyl chloride, and methyl bromide; the molar ratio of toluene or benzene to the methylating agent is from 1/10 to 20/1; the methylation reaction is carried out it 200° to 650° C., atmospheric pressure up to 20 kilograms per square centimeter (gauge), and weight hourly space velocity (WHSV) of 0.1 to 50 per hour.

19. The process as claimed in claim 10, wherein the methylation is carried out by the use of one or more methylating agents selected from methanol, dimethyl ether, methyl chloride, and methyl bromide; the molar ratio of toluene or benzene to the methylating agent if from 1/10 to 20/1; the methylation reaction is carried out at 200° to 650° C., atmospheric pressure up to 20 kilograms per square centimeter (gauge), and weight hourly space velocity (WHSV) of 0.1 to 50 per hour.

20. The process as claimed in claim 12, wherein the methylation is carried out by the use of one or more methylating agents selected from methanol, dimethyl ether, methyl chloride, and methyl bromide; the molar ratio of toluene or benzene to the methylating agent is from 1/10 to 20/1; the methylation reaction is carried out at 200° to 650° C., atmospheric pressure up to 20 kilograms per square centimeter (gauge), and weight hourly space velocity (WHSV) of 0.1 to 50 per hour.

* * * * *